(12) United States Patent
Son et al.

(10) Patent No.: US 8,765,197 B2
(45) Date of Patent: Jul. 1, 2014

(54) EXTRACT OF HERBAL AND COMPOSITION CONTAINING THE SAME

(75) Inventors: Mi Won Son, Seongnam-si (KR); Sang Jin Choi, Yongin-si (KR); Chong Hwan Cho, Yongin-si (KR); Nam Joon Baek, Incheon (KR); Tae Ho Lee, Seongnam-si (KR); Jae Keol Rhee, Suwon-si (KR); Soon Hoe Kim, Suwon-si (KR); Moo Hi Yoo, Seoul (KR); Mi Rim Jin, Seoul (KR); Jin Pub Son, Seoul (KR)

(73) Assignee: Dong-A-Pharm, Co., Ltd., Seoul (KR)

( * ) Notice: Subject to any disclaimer, the term of this patent is extended or adjusted under 35 U.S.C. 154(b) by 520 days.

(21) Appl. No.: 12/224,327

(22) PCT Filed: Feb. 27, 2007

(86) PCT No.: PCT/KR2007/000990
§ 371 (c)(1),
(2), (4) Date: Aug. 25, 2008

(87) PCT Pub. No.: WO2007/100203
PCT Pub. Date: Sep. 7, 2007

(65) Prior Publication Data
US 2009/0186108 A1 Jul. 23, 2009

(30) Foreign Application Priority Data
Feb. 28, 2006 (KR) .................. 10-2006-0019261

(51) Int. Cl.
*A61K 36/00* (2006.01)
*A61K 36/31* (2006.01)

(52) U.S. Cl.
USPC ............ 424/755; 424/725; 424/773; 424/776

(58) Field of Classification Search
None
See application file for complete search history.

(56) References Cited

U.S. PATENT DOCUMENTS 3,843,788 A * 10/1974 Iwasa et al. .................. 424/773

FOREIGN PATENT DOCUMENTS

| CN | 1140071 | * | 1/1997 | |
|---|---|---|---|---|
| CN | 1140071 A | * | 1/1997 | ............. A61K 35/78 |
| KR | 2001-0075910 | | 8/2001 | |
| WO | 03/086441 | | 10/2003 | |

OTHER PUBLICATIONS

The Herbal Encyclopedia. Retrieved from the internet. <http://web.archive.org/web/20030210135948/http://www.naturalark.com/herbcomb.html>. web archive date Feb. 10, 2003. Retrieved on Oct. 24, 2010. pp. 1-9.*
Lorenzo et al. Diagnosis and Management of Intestinal Motility Disorders. Seminars in Pediatric Surgery. 2010. 19, pp. 50-58.*
www. digestivedistresrs.com. A Fact Sheet for Families: Gastrointestinal Motility Disorders. Nov. 28, 2007. Retrieved from the internet. Retrieved on Oct. 23, 2010. pp. 1-2.*
Katrak et al. Materia Medica of India and their Therapeutics. Caxton Works. 1903. p. 70.*
viable-herbal.com. web archive date Jan. 24, 2010. Retrieved from the internet. <http://web.archive.org/web/20000124113842/http://viable-herbal.com/herbology1/herbs42.htm>. Retrieved on Oct. 24, 2010. pp. 1-4.*
Zhu. Chinese Materia Media: Chemistry, Pharmacology and Applications. CRC Press. 1998. p. 245.*
Cazes. Encyclopedia of Chromatography. vol. 2. CRC Press. 2005. pp. 1256.*
Jeoung Seob Kim et al., *Inhibitory Effects of Some Herbal Extracts on the Acetylcholinesterase (AChE) In Vitro*, 33 Kor. J. Pharmacogn. 211 (2002).
Kwon-il Seo et al., *Antimicrobial Activities in the Water Extract of Mustard Seed Fractionated by Solvents*, 4 Kor. J. Post-Harvest Sci. Technol. Agri. Products 295 (1997).
Yeon Hoi Heo & Sang Kook Lee, *Potential Induction of Quinone Reductase Activity of Natural Products in Cultured Murine Hepalclc7 Cells*, 7 Natural Product Sciences 38 (2001).

* cited by examiner

*Primary Examiner* — Chris R Tate
*Assistant Examiner* — Russell Fiebig
(74) *Attorney, Agent, or Firm* — Vorys, Sater, Seymour and Pease LLP; Mihsun Koh

(57) ABSTRACT

The present invention relates to herbal extracts of *Sinapis* Semen, *Corydalis* Tuber, *Pharbitidis* Seed, and *Strychni Ignatii* Semen, and a composition containing the same for treating and preventing gastrointestinal motility disorder. The extracts of the present invention have a remarkable effect of promoting gastrointestinal motility through $HT_3$ receptor antagonism and/or $HT_4$ receptor antagonism.

8 Claims, 3 Drawing Sheets

A   B   C   D   mixed
A: Strychni Ignatii Semen
B: Sinapis Semen
C: Pharbitidis Seed
D: Corydalis Tuber A   B   C   D   mixed
A: Strychni Ignatii Semen
B: Sinapis Semen
C: Pharbitidis Seed
D: Corydalis Tuber

SEQUENCE LISTING

<160> NUMBER OF SEQ ID NOS: 2

<210> SEQ ID NO 1
<211> LENGTH: 1506
<212> TYPE: DNA
<213> ORGANISM: Artificial Sequence
<220> FEATURE:
<223> OTHER INFORMATION: Sequence of HTR03A0000

<400> SEQUENCE: 1

| | | |
|---|---|---|
| gctagcgttt aaacttaagc ttggtaccga gctcggatcc accatgctgc tgtgggtcca | 60 |
| gcaggcgctg ctcgccttgc tcctccccac actcctggca cagggagaag ccaggaggag | 120 |
| ccgaaacacc accaggcccg ctctgctgag gctgtcggat taccttttga ccaactacag | 180 |
| gaagggtgtg cgccccgtga gggactggag gaagccaacc accgtatcca ttgacgtcat | 240 |
| tgtctatgcc atcctcaacg tggatgagaa gaatcaggtg ctgaccacct acatctggta | 300 |
| ccggcagtac tggactgatg agtttctcca gtggaaccct gaggactttg acaacatcac | 360 |
| caagttgtcc atcccacgg acagcatctg gtcccggac attctcatca atgagttcgt | 420 |
| ggatgtgggg aagtctccaa atatcccgta cgtgtatatt cggcatcaag gcgaagttca | 480 |
| gaactacaag ccccttcagg tggtgactgc ctgtagcctc gacatctaca acttccccttt | 540 |
| cgatgtccag aactgctcgc tgaccttcac cagttggctg cacaccatcc aggacatcaa | 600 |
| catctctttg tggcgcttgc cagaaaaggt gaaatccgac aggagtgtct tcatgaacca | 660 |
| gggagagtgg gagttgctgg gggtgctgcc ctactttcgg gagttcagca tggaaagcag | 720 |
| taactactat gcagaaatga agttctatgt ggtcatccgc cggcggcccc tcttctatgt | 780 |
| ggtcagcctg ctactgccca gcatcttcct catggtcatg gacatcgtgg gcttctacct | 840 |
| gccccccaac agtggcgaga gggtctcttt caagattaca ctcctcctgg gctactcggt | 900 |
| cttcctgatc atcgtttctg acacgctgcc ggccactgcc atcggcactc ctctcattgg | 960 |
| tgtctacttt gtggtgtgca tggctctgct ggtgataagt ttggccgaga ccatcttcat | 1020 |
| tgtgcggctg gtgcacaagc aagacctgca gcagcccgtg cctgcttggc tgcgtcacct | 1080 |
| ggttctggag agaatcgcct ggctactttg cctgagggag cagtcaactt cccagaggcc | 1140 |
| cccagccacc tcccaagcca ccaagactga tgactgctca gccatgggaa accactgcag | 1200 |
| ccacatggga ggaccccagg acttcgagaa gagcccgagg gacagatgta gccctccccc | 1260 |
| accacctcgg gaggcctcgc tggcggtgtg tgggctgctg caggagctgt cctccatccg | 1320 |
| gcaattcctg gaaaagcggg atgagatccg agaggtggcc cgagactggc tgcgcgtggg | 1380 |
| ctccgtgctg acaagctgc tattccacat ttacctgctg gcggtgctgg cctacagcat | 1440 |
| caccctggtt atgctctggt ccatctggca gtacgcttga ctcgagtcta gagggcccgt | 1500 |
| ttaaac | 1506 |

<210> SEQ ID NO 2
<211> LENGTH: 1259
<212> TYPE: DNA
<213> ORGANISM: Artificial Sequence
<220> FEATURE:
<223> OTHER INFORMATION: Sequence of HTR0400000

<400> SEQUENCE: 2

| | | |
|---|---|---|
| gctagcgttt aaacttaagc ttggtaccga gctcggatcc actagtccag tgtggtggaa | 60 |
| ttcaccatgg acaaacttga tgctaatgtg agttctgagg agggtttcgg tcagtggaga | 120 |
| aaggtggtgc tgctcacgtt tctctcgacg gttatcctga tggccatctt ggggaacttg | 180 |

-continued

```
ctggtgatgg tggctgtgtg ctgggacagg cagctcagga aaataaaaac aaattatttc    240
attgtatctc ttgcttttgc ggatctgctg gtttcggtgc tggtgatgcc ctttggtgcc    300
attgagctgg ttcaagacat ctggatttat ggggaggtgt tttgtcttgt tcggacatct    360
ctggacgtcc tgctcacaac ggcatcgatt tttcacctgt gctgcatttc tctggatagg    420
tattacgcca tctgctgcca gcctttggtc tataggaaca agatgacccc tctgcgcatc    480
gcattaatgc tgggaggctg ctgggtcatc cccacgttta tttcttttct ccctataatg    540
caaggctgga ataacattgg cataattgat ttgatagaaa agaggaagtt caaccagaac    600
tctaactcta cgtactgtgt cttcatggtc aacaagccct acgccatcac ctgctctgtg    660
gtggccttct acatcccatt tctcctcatg gtgctggcct attaccgcat ctatgtcaca    720
gctaaggagc atgcccatca gatccagatg ttacaacggg caggagcctc ctccgagagc    780
aggcctcagt cggcagacca gcatagcact catcgcatga ggacagagac caaagcagcc    840
aagaccctgt gcatcatcat gggttgcttc tgcctctgct gggcaccatt ctttgtcacc    900
aatattgtgg atcctttcat agactacact gtccctgggc aggtgtggac tgctttcctc    960
tggctcggct atatcaattc cgggttgaac ccttttctct acgccttctt gaataagtct   1020
tttagacgtg ccttcctcat catcctctgc tgtgatgatg agcgctaccg aagaccttcc   1080
attctgggcc agactgtccc ttgttcaacc acaaccatta atggatccac acatgtacta   1140
agggatgcag tggagtgtgg tggccagtgg gagagtcagt gtcacccgcc agcaacttct   1200
cctttggtgg ctgctcagcc cagtgacact tagctcgagt ctagagggcc cgtttaaac   1259
```

EXTRACT OF HERBAL AND COMPOSITION CONTAINING THE SAME

TECHNICAL FIELD

This invention relates to one or more herbal extracts selected from the group consisting of *Sinapis* Semen, *Corydalis* Tuber, *Pharbitidis* Seed and *Strychni Ignatii* Semen and the composition containing the same for treating and preventing gastrointestinal motility disorder.

BACKGROUND ART

Functional dyspepsia is not pathological or biochemical organic lesion but functional symptoms accompanied by continuous discomfort or pain in the upper abdominal area. Medically it means various symptoms associated with the continuous and repetitive discomfort or pain confined to the upper abdomen. Specifically non-ulcerative dyspepsia, one of the functional dyspepsia, includes all the symptoms of digestive system including satiety after a meal, anorexia, abdominal distention, an early sense of satiety, belching, discomfort or pain in the upper abdomen, brash, nausea, vomiting, gastric reflux, heartburn and others. Its pathophysiology is not clearly known yet (Panganamamula et al., *Functional (Nonulcer) Dyspepsia*, Current Treatment Options in Gastroenterology, 5, pp. 153-160, 2002).

Functional dyspepsia is diagnosed based on various dyspepsia symptoms without apparent organic lesion, so cure is not simple and most symptoms alternate between improvement and deterioration affected severely by diet and stress. These pathological mechanisms act together manifesting one or usually multiple symptoms.

Representative functional dyspepsia treatment includes prokinetic drugs such as domperidone, metoclopramide, levosulpride, mosapride, itopride and erythromycin. As brash and ulcer are the representative symptoms of functional dyspepsia, gastric acid suppressant and antacid are used for the treatment but these including $H_2$ antagonist drugs usually have temporary efficacy (Vincenzo Stanghellini et al., Delayed Gastric Emptying in Functional Dyspepsia, Current Treatment Options in Gastroenterology, 7, 259-264, 2004).

Recently the development of new prokinetic agent is centered on serotonergic modulating drugs as serotonin (5-hydroxytrypamine, 5-HT) plays a central role in gastrointestinal peristaltic movement, and 80% of serotonin resides in gastrointestinal tract, especially 95% of which is distributed in intra bowel secretion cells in the small intestine.

Specific agonist and antagonist drugs for 5-HT related receptors are being developed and 5-HT4agonist is under development as a cure for functional dyspepsia as well as constipation because it facilitates prokinetic action with increased gastric contractive force and propulsive pressure. $5\text{-HT}_3$ antagonist is effective for suppressing vomiting and diminishing visceral hypersensitivity, and $5\text{-HT}_{1p}$ agonist is being developed as functional dyspepsia cure for its relaxing mechanism in fundus ventriculi (Robin spiller, *Serotonergic modulating drugs for functional gastrointestinal disease*, J Clin Pharmacol, 54, pp. 11-20, 2002).

Specifically $5\text{-HT}_3$ receptor antagonist, granisetron, reduces rectum sensitivity in irritable bowel syndrome patients, and ondansetron is not effective for irritable bowel syndrome patients but reduces vomiting and gastric sensitivity caused by expansion when fat goes into duodenum in healthy people. Cilansetron improves gastrointestinal sensitivity modulation and the adaptability of digestive duct for gastric expansion, blocks the excitable $5\text{-HT}_3$ receptor associated with peristaltic movement, and raises jejunal fluid absorption. However tropisetron, ondansetron and most other $5\text{-HT}_3$ receptor antagonists improve the gastrointestinal fasting delay symptom in rats but the effect is not conclusive in other species including humans.

Cisapride is one of the prokinetic drugs used effectively for cure of functional dyspepsia, is $5\text{-HT}_4$ receptor agonist and $5\text{-HT}_3$ receptor antagonist, and is recognized as having a statistically significant effect compared to other drugs. The response rate of cisapride is 50-82%, higher than the rate of placebo which is 27-53%, and it is reported to be effective in more than 70% of the cases when administered for 4 to 8 weeks. It is also reported that cisapride has efficacy for the concomitant disease of irritable bowel syndrome and also improves the symptoms of patients who do not respond to the cure using dopamine antagonist of levosulpride and domperidone. After it was approved as a drug for gastro-esophageal reflux disease in 1993, it led the market with an annual revenue of 40 billion (world market: 1.3 billion dollars) but in July 2000 its sales was banned.

On the other hand, another serotonin receptor 5-HT1 B/D agonist, triptans, is effective at the dose used for migraine for gastrointestinal movement and sensitive gastro-intestine. Sumatriptan is reported to delay emptying the gastric contents but its effect is known to improve the upper abdominal symptoms as it improves the modulation of fundus ventriculi and lowers the gastrointestinal expansion response in the actual functional dyspepsia patients.

5-HT4 receptor agonist, whish is one of the newly used prokenetic drugs for functional dyspepsia cure, improves the symptoms without increasing the tension at the fundus ventriculi. Cisapride, one of the $5\text{-HT}_4$ receptor agonist, is effective to facilitate stomach emptying, and as to the duodenum or intragastric pressure wavelength (>6 cm), the threshold value of recognizing gastric expansion is increased not only in patients but also in healthy humans as well. 5-HT4 receptor agonist drugs include tegaserod and prucalopride but they are under clinical study and target disorders in the lower digestive system (Fraser R J, Postprandial antropyloroduodenal motility and gastric emptying in gastroparesis—effects of cisapride, Gut, 35(2), p. 172-8, 1994; Talley N.J., New and emerging treatments for irritable bowel syndrome and functional dyspepsia, *Expert Opin Emerg Drugs*, 7(1), p. 91-8, 2002).

Meanwhile, Korean mustard of *Sinapis* Semen is the ripe seeds of *Brassica juncea* Cosson of the Cruciferae family, contains Sinalbin, Sinapine and fatty oil, and is effective to discharge phlegm and stimulate skin. (The Korean Pharmacopoedia V Part 2 pp 453-454).

*Corydalis* Tuber is *Corydalis ternata* Nakai and other tuberous plants of the Papaveraceae family, contains Berberine, 1-Canadine, Protopine and 1-tetrahydrocoptisine, and has analgesic, sedative, antispasmodic, antiemetic and ACTH hyper-secretion actions. (The Korean Pharmacopoedia V Part 2 pp 664)

*Pharbitidis* Seed s are the seeds of *Pharbitis nil* Choisy of the Convolvulaceae family, contain roughly 11% of fatty oil and 2% of pharbitin which is resinous glucoside, and are known to have easy defecation, diuretic and insecticidal effects. (The Korean Pharmacopoedia V Part 2 pp 651).

*Strychni Ignatii* Semen is the seeds of *Strychnos ignatii* Bergius of the Loganiaceae family, contains Strychnine, Brucine, Vomicine, a-Colubrine, β-Colubrine and Loganine, and has CNS exciting, stomachic, antifungal, anti-inflammatory and analgesic effects. (Oriental Herb (galenicals) Standard Annotation, pp 175, The Korean Pharmacopoedia V Part 2 pp 633-634)

However these galenicals have been used as oriental medicine mixed with other various herbs, so there has been no report on its specific prokinetic mechanism of action.

With the background, to identify the prokinetic herb that have the treatment and preventive effects for functional dyspepsia and irritable bowel syndrome, the inventor performed the activation test for 5-HT3 and 5-HT5 receptors which correspond to prokinetic trigger points and identified the candidate herb activating the receptors. Based on this, appropriate herb extracts have been found through animal model experiments for functional dyspepsia.

Also, the inventor found that the herb extracts of this invention are 5-HT3 antagonist facilitating antiemetic and gastric emptying, and suppressing visceral hypersensitivity, and are 5-HT4 receptor agonist showing prokinetic and treatment effects for irritable bowel syndrome accompanied by constipation and chronic colitis. The invention was completed by confirming the fact that the herbs individually or in combination have the cure effect for functional dyspepsia and irritable bowel syndrome.

DISCLOSURE

Technical Problem

The object of the present invention is to provide herbal extracts, and a composition containing the same as an active ingredient, for preventing and treating gastrointestinal motility disorder.

Technical Solution

The present invention provides one or more herbal extracts of *Sinapis* Semen, *Corydalis* Tuber, *Pharbitidis* Seed and *Strychni Ignatii* Semen.

In the present, 'a herbal extract' means a herbal extract and/or a mixture of herbal extracts, if the herbal extract is not modified by the other words or phrases.

The present invention is explained in detail below.

The present invention provides a herbal extract of *Sinapis* Semen, *Corydalis* Tuber, *Pharbitidis* Seed and *Strychni Ignatii* Semen.

And, the present invention provides a mixture of two or more herbal extracts of *Sinapis* Semen, *Corydalis* Tuber, *Pharbitidis* Seed and *Strychni Ignatii* Semen.

The present mixture includes a mixture of the herbal extracts of *Sinapis* Semen and *Corydalis* Tuber. Preferably, the mixture has the mixture ratio of the herbal extract of *Sinapis* Semen: the herbal extract of *Corydalis* Tuber from 1:1 to 10:1 by weight (w/w).

The present mixture includes a mixture of the herbal extracts of *Sinapis* Semen and *Pharbitidis* Seed Preferably, the mixture has the mixture ratio of the herbal extract of *Sinapis* Semen: the herbal extract of *Pharbitidis* Seed from 1:1 to 30:1 by weight (w/w).

The present mixture includes a mixture of the herbal extracts of *Corydalis* Tuber and *Pharbitidis* Seed. Preferably, the mixture has the mixture ratio of the herbal extract of *Corydalis* Tuber: the herbal extract of *Pharbitidis* Seed from 1:1 to 10:1 by weight (w/w).

The present mixture includes a mixture of the herbal extracts of *Corydalis* Tuber and *Strychni Ignatii* Semen. Preferably, the mixture has the mixture ratio of the herbal extract of *Corydalis* Tuber: the herbal extract of *Strychni Ignatii* Semen from 3:1 to 1:3 by weight (w/w).

The present mixture includes a mixture of the herbal extracts of *Pharbitidis* Seed and *Strychni Ignatii* Semen. Preferably, the mixture has the mixture ratio of the herbal extract of *Pharbitidis* Seed: the herbal extract of *Strychni Ignatii* Semen from 1:1 to 1:10 by weight (w/w).

The present mixture includes a mixture of the herbal extracts of *Sinapis* Semen, *Corydalis* Tuber, and *Pharbitidis* Seed Preferably, the mixture has the mixture ratio of the herbal extract of *Sinapis* Semen: the herbal extract of *Corydalis* Tuber: the herbal extract of *Pharbitidis* Seed of (1~30): (1~10): 1 by weight (w/w).

The present mixture includes a mixture of the herbal extracts of *Sinapis* Semen, *Corydalis* Tuber, *Pharbitidis* Seed, and *Strychni Ignatii* Semen. Preferably, the mixture has the mixture ratio of the herbal extract of *Sinapis* Semen: the herbal extract of *Corydalis* Tuber: the herbal extract of *Strychni Ignatii* Semen: the herbal extract of *Pharbitidis* Seed of (1~30): (1~10): 1: (1~10) by weight (w/w).

And, the herbs of the present invention include congener herbs that are known in the art to be useful for preventing and treating the same disorder as specified in the present invention.

Also, the present invention provides a preparation method of the herbal extracts of the present invention, characterized in that a herb selected from the group consisting of *Sinapis* Semen, *Corydalis* Tuber, *Pharbitidis* Seed and *Strychni Ignatii* Semen is extracted by water, a lower alcohol of C1~C4, or a mixture thereof. Preferably, the selected herb is extracted one to five times at 45~75° C. for 65~80 hours.

The present invention also provides a preparation method of one or more extracts selected from the group consisting of *Sinapis* Semen, *Corydalis* Tuber, *Pharbitidis* Seed and *Strychni Ignatii* Semen, an extract soluble in polar solvent, and an extract soluble in non-polar solvent, comprising the first step that one or more herbs selected from the group consisting of *Sinapis* Semen, *Corydalis* Tuber, *Pharbitidis* Seed and *Strychni Ignatii* Semen are extracted by water, a lower alcohol of C1~C4, or a mixture thereof, filtered, and concentrated to obtain a herbal extract; the second step that the herbal extract of the first step is treated sequentially with hexane, chloroform, and ethylacetate to collect extracts soluble in non-polar solvent; and the third step that the extracts soluble in non-polar solvent of the second step are treated with water, methanol, butanol or mixture thereof, to obtain the herbal extracts soluble in polar solvent.

The present extracts include an extract, an extract soluble in polar solvent, or an extract soluble in non-polar solvent. The extract is extracted by a solvent selected from water, a lower alcohol of C1~C4, or a mixture thereof, preferably ethanol. And, the extract soluble in polar solvent is extracted from a solvent selected from water, methanol, butanol or a mixture thereof, preferably butanol. The extract soluble in non-polar solvent is extracted from a solvent selected from hexane, chloroform, and ethylacetate.

In the present invention, one or more herbal extracts selected from the group consisting of *Sinapis* Semen, *Corydalis* Tuber, *Pharbitidis* Seed and *Strychni Ignatii* Semen can be obtained by the following processes.

Firstly, after *Sinapis* Semen, *Corydalis* Tuber, *Pharbitidis* Seed or *Strychni Ignatii* Semen is washed and dried, the dried herb is milled to make a milled herb by a mill, and the milled herb is grinded to powder by a grinder. The dried herb or powder is put in water, a lower alcohol such as ethanol or methanol (preferably ethanol), or a mixture thereof, in the amount of 1~25 times the weight of the dried herb or powder (preferably 5~15times). And, they were extracted by hydrothermal extraction, cold precipitated extraction, refluxing-cooling extraction, or ultrasonic extraction [preferably extracted one to five times by using the hydrothermal extraction at 20~100° C. (preferably 45~75° C.) for about 1~100 hours (preferably 65~80 hours)], filtered under vacuum, and lyophilized to obtain the herbal extract from *Sinapis* Semen, the herbal extract from *Corydalis* Tuber, the herbal extract from *Pharbitidis* Seed, and the herbal extract from *Strychni Ignatii* Semen.

Each of the herbal extract from *Sinapis* Semen, the herbal extract from *Corydalis* Tuber, the herbal extract from *Pharbitidis* Seed, and the herbal extract from *Strychni Ignatii* Semen was suspended in water and extracted by using solvents in the order of chloroform, ethylacetate, and butanol to obtain an extract soluble in polar solvent and an extract soluble in non-polar solvent of the present invention. Particularly, the extract soluble in polar solvent and the extract soluble in non-polar solvent of the present invention were obtained by a method comprising the first step in which each of the herbal extract from *Sinapis* Semen, the herbal extract from *Corydalis* Tuber, the herbal extract from *Pharbitidis* Seed, and the herbal extract from *Strychni Ignatii* Semen (the extracts obtained by hydrothermal extraction) was added to hexane to obtain a hexane-soluble extract and a water-soluble extract; the second step in which the water-soluble extract obtained in the first step was extracted by chloroform to obtain a chloroform-soluble extract and a water-soluble extract; the third step in which the water-soluble extract obtained in the second step was extracted by ethylacetate to obtain an ethylacetate-soluble extract and a water-soluble extract; and the fourth step in which the water-soluble extract obtained in the third step was extracted by butanol to obtain a butanol-soluble extract and a water-soluble extract.

The present invention provides a composition for preventing and treating gastrointestinal motility disorder, comprising the herbal extracts of the present invention as an active ingredient and pharmaceutically acceptable carrier, diluent, or filler.

The composition of the present invention contains the extracts in 0.01 to 80% weight of the total weight of the composition [preferably, 1 to 50% (w/w)].

In preparing the present composition, some elements can be added to, or taken out from, the present herbal extract, and the mixing ratios may be changed.

Here, gastrointestinal motility disorder is characterized as a disease caused by hyperactivity of $5\text{-}HT_3$ receptor and/or $5\text{-}HT_4$ receptor antagonism.

The gastrointestinal motility disorder includes functional dyspepsia such as early satiety, pain, epigastric distress, a false sense of satiety, heartburn, nausea and vomiting; ulcerative dyspepsia; non-ulcerative dyspepsia; reflux oesophagitis; paralysis of gastric motility; constipation; irritable bowel syndrome; hypersensitive colitis; diabetic gastrointestinal motility disorder; gastrointestinal motility disorder originated chemotherapy; and intestinal atresia originated motility disorder of digestive tract and myotonic dystrophy originated gastric intestinal motility disorder.

The irritable colitis includes general colitis, irritable colitis accompanied by constipation or diarrhea.

The present composition including the herb extracts may further include appropriate carrier, excipient or diluent.

Carrier, excipient and diluent that can be included in the composition of the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microchrystalline cellulose, polyvinyl pyrrolidone, water, methylhydroxybenzoate, prophylhydroxybenzoate, talc, magnesium stearate or mineral oil.

Also, the composition of the present invention can be prepared into oral medicine like powder, granulum, tablet, capsule, suspension, emulsion, syrup and aerosol; external medicine; or suppository or sterile injection solution.

Specifically, when prepared into medicines, diluent or excipient such as generally used priming agents, expanders, bonding agents, humectants, disintegrators or detergents can be added. Solid products for oral administration include tablets, pills, powder, granulum, capsules and others. The herb composition can be mixed with at least one or more excipients like starch, calcium carbonate, sucrose, lactose or gelatin. Not only the simple excipient but also lubricants like magnesium stearate or talc can be used. For liquid oral products, suspension, contents agent, emulsion and syrup can be used, but commonly used simple diluents like water and liquid paraffin as well as various excipients such as humectants, sweetening agents, odorants or preservatives can also be used. Non-oral administrative products include sterile aqueous suspension, non-aqueous solvent, suspension, emulsion, freeze-dried products, and suppository. For non-aqueous solvent and suspension, propylene glycol, polyethylene glycol, vegetable oil like olive oil, or injectable ester such as ethyloleate can be used. For the base of suppository, witepsol, macrogol, tween 61, cacao butter, laurin fat, glycerol gelatin and others can be used.

Also, the present invention provides a use of the herb extracts of the present invention for cure and prevention of gastrointestinal motility disorder.

Moreover, the present invention provides a treatment method of gastrointestinal motility disorder by administering the pharmaceutical composition with the herb extracts of the present invention in the effective dosage to mammals including humans.

The administration dose of the composition of the present invention including the herb extracts may vary depending on the age, gender or body weight of a patient. However, generally, the dried powder of the extracts can be administered in single or multiple doses in the amount of 0.01 to 10 g/Kg, preferably 5 g/Kg a day. The dose can be adjusted depending on administration path, severity of disease, gender, body weight, age, health status, diet, administration time and method, and excretion rate. Therefore the above dose by no means limits the scope of the present invention.

The pharmaceutical composition of the present invention can be administered to mammals like rat, mouse, cattle or humans through a variety of paths. For instance, it can be administered orally, through rectum, or by venous, muscular, subcutaneous, uterine dura mater or intracerebroventricular injection.

The herb extracts of the present invention can be safely used for a long time for the purpose of prevention since they have little toxicity or adverse effect.

To confirm the prokinetic and anti-dyspepsia efficacy of the herb extracts, the present inventor tested their affinity to, antagonism against and agonism to the receptors of $5\text{-}HT_3$ and $5\text{-}HT_4$, and verified their selective and outstanding efficacy. Also, to identify the proper ratio of the herb extracts, various in vivo experiments using many functional dyspepsia pathologies on animal models were performed, and the remarkable effects of the extracts have been verified.

To prevent and improve the gastrointestinal motility disorder, the present invention provides health functional foods with one or more extracts selected from the group of Korean mustard, *Corydalis* Tuber, *Pharbitidis* Seed and *Strychni Ignatii* Semen, and food additives allowed in sitology.

The health functional foods used in the present invention have the characteristics of health function food ingredients listed in the Korean FDA Notice 2004-12 based on the functions and safety on humans for newly defining the Health Function Food Act of 2002.

The present invention also provides a health care food for preventing and improving gastrointestinal motility disorder containing two or more herbal extracts selected from the group consisting of *Sinapis* Semen, *Corydalis* Tuber, *Pharbitidis* Seed and *Strychni Ignatii* Semen, and sitologically acceptable addition agents.

The present invention provides a health care food for preventing and improving gastrointestinal motility disorder containing a mixture of the herbal extract of *Sinapis* Semen, the herbal extract of *Corydalis* Tuber, and the herbal extract of *Pharbitidis* Seed, and sitologically acceptable addition agents. Preferably, in the mixture, the mixture ratio of the herbal extract of *Sinapis* Semen: the herbal extract of *Corydalis* Tuber: the herbal extract of *Pharbitidis* Seed is (1~30): (1~10):1 by weight (w/w).

The present invention provides a health care food for preventing and improving gastrointestinal motility disordercontaining a mixture of the herbal extract of *Sinapis* Semen, the herbal extract of *Corydalis* Tuber, the herbal extract of *Pharbitidis* Seed, and the herbal extract of *Strychni Ignatii* Semen, and sitologically acceptable addition agents. Preferably, in the mixture, the mixture ratio of the herbal extract of *Sinapis* Semen: the herbal extract of *Corydalis* Tuber: the herbal extract of *Strychni Ignatii* Semen: the herbal extract of *Pharbitidis* Seed is (1~30): (1~10): 1: (1~10) by weight (w/w).

The present invention provides a health care food for preventing and improving gastrointestinal motility disorder containing a mixture of the herbal extract of *Sinapis* Semen and the herbal extract of *Corydalis* Tuber, and sitologically acceptable addition agents. Preferably, in the mixture, the mixture ratio of the herbal extract of *Sinapis* Semen: the herbal extract of *Corydalis* Tuber is 1:1 to 10:1 by weight (w/w).

The present invention provides a health care food for preventing and improving gastrointestinal motility disorder containing a mixture of the herbal extract of *Sinapis* Semen and the herbal extract of *Pharbitidis* Seed, and sitologically acceptable addition agents. Preferably, in the mixture, the mixture ratio of the herbal extract of *Sinapis* Semen: the herbal extract of *Pharbitidis* Seed is 1:1 to 30:1 by weight (w/w).

The present invention provides a health care food for preventing and improving gastrointestinal motility disorder containing a mixture of the herbal extract of *Corydalis* Tuber and the herbal extract of *Pharbitidis* Seed, and sitologically acceptable addition agents. Preferably, in the mixture, the mixture ratio of the herbal extract of *Corydalis* Tuber: the herbal extract of *Pharbitidis* Seed is 1:1 to 10:1 by weight (w/w).

The present invention provides a health care food for preventing and improving gastrointestinal motility disorder containing a mixture of the herbal extract of *Corydalis* Tuber and the herbal extract of *Strychni Ignatii* Semen, and sitologically acceptable addition agents. Preferably, in the mixture, the mixture ratio of the herbal extract of *Corydalis* Tuber: the herbal extract of *Strychni Ignatii* Semen is 3:1 to 1:3 by weight (w/w).

The present invention provides a health care food for preventing and improving gastrointestinal motility disorder containing a mixture of the herbal extract of *Pharbitidis* Seed and the herbal extract of *Strychni Ignatii* Semen, and sitologically acceptable addition agents.

Preferably, in the mixture, the mixture ratio of the herbal extract of *Pharbitidis* Seed: the herbal extract of *Strychni Ignatii* Semen is 1:1 to 1:10 by weight (w/w).

On the other hand, the composition including the herb extracts of the present invention can be used in various forms of drugs, food, and drinks for prokinetic effect. The herb extracts of the present invention can be added to various foods like drinks, gum, tea, vitamin complex, and health supplementary food, and can be used in the form of pill, powder, granule, infusion, tablet, capsule, or drink.

The dose of the herb extracts in food or drinks for the health food composition of the present invention is generally 0.01 to 15 weight % of the total food weight, preferably 0.1 to 10 weight %. For health drink composition, 0.1 to 30 g, preferably 0.2 to 5 g, of the herb extracts can be added to 100 ml.

For the health drink composition, only the herb extracts are necessary ingredients with specific ratio, and there are no special restrictions on the liquid ingredients. Like common drinks, various kinds of flavors and natural carbohydrate can be added.

The examples of the above mentioned natural carbohydrate would be mono-saccharides, disaccharides such as glucose and fructose, polysaccharides such as maltose and sucrose, general sugar such as dextrin and cyclodexterin, and sugar alcohol such as xylitol, sorbitol, and erithritol. In addition to the above mentioned flavors, natural flavors (thaumatin, stevia extract (i.e. rebaudiosid A, glycyrrhizin)) and synthetic flavors (i.e. saccharides, aspartame) can be used. For the above natural carbohydrate composition, generally 1 to 20 g per 100 ml, preferably 5 to 12 g, is used.

Other than the above, the composition of the present invention may contain various nutrients, vitamins, minerals (electrolyte), synthetic and natural flavoring agents, colorants, extenders (such as cheese, chocolate), pectic acid and pectinate, alginic acid and alginate, organic acid, protective colloid thickening agents, pH modulator, stabilizer, preservatives, glycerin, alcohol, carbonator used in carbonated drinks and others. Additionally, the composition of the present invention can contain the flesh of fruits to produce natural fruit juice, fruit juice drinks, and vegetable drinks. These ingredients can be used alone or in combination. The ratios of these additives are not crucial, but generally 0 to 20 weight/percent per 100 weight of the composition of the present invention is used.

Advantageous Effects

The extracts of the present invention or a mixture thereof may be used as a pharmaceutical composition for preventing and treating gastrointestinal motility disorder and a health functional food to facilitate gastrointestinal motility through $HT_3$ receptor antagonism and/or $HT_4$ receptor agonism.

MODE FOR INVENTION

Figure 1:
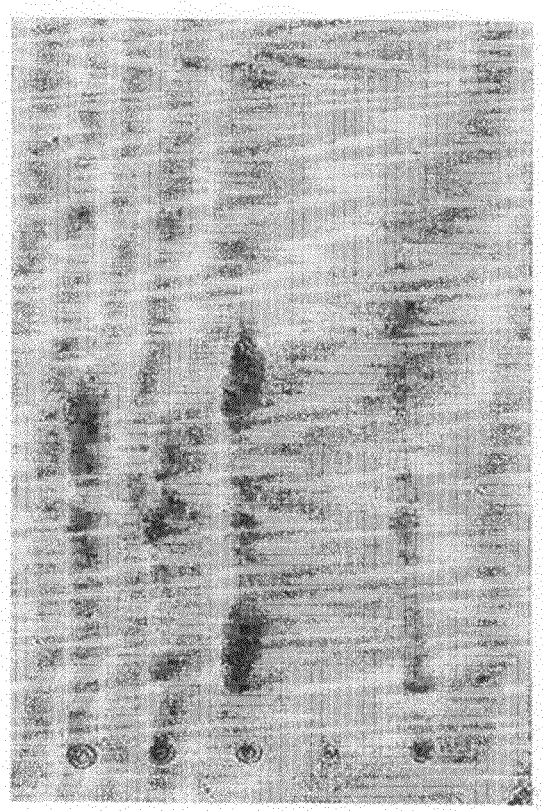
FIG. 1 is a schematic drawing illustrating the analytic results of thin liquid chromatography (TLC) of ethanol extracts of *Sinapis* Semen, *Corydalis* Tuber, *Pharbitidis* Seed and *Strychni Ignatii* Semen using $H_2SO_4$.

The present invention is explained by the following examples and experimental examples in more detail.

The following examples are intended to further illustrate the present invention, and the scope of the present invention cannot be limited thereby in any way.

r.t means a room temperature in the present invention.

EXAMPLE 1

Preparation of Herbal Extracts of the Present Invention

1-1. Preparation of an extract of *Sinapis* Semen

*Sinapis* Semen was bought at a Chinese herb medicine shop of Kyung-dong market, washed to remove adulterations, and dried to use at the experiment. And, the dried herb was milled by a mill, and 20 g of the milled *Sinapis* Semen was put in 0%, 15%, 30%, 50%, 70%, 85% and 96% ethanol-water (160 ml) and stirred at room temperature for 72 h. Then, the resulting mixture was extracted, filtered, and concentrated at 55~65° C. under a low pressure, and freeze-dried to obtain an extract of *Sinapis* Semen (1.04~3.1 g)(Table 1: Yields of extracts of *Sinapis* Semen as a kind of solvent).

TABLE 1

| Amount of a herb | Amount solvent | Amount of solvent | wash | Extraction temperature | Extraction time | Obtained amount (g) | Yield (%) |
| --- | --- | --- | --- | --- | --- | --- | --- |
| 20 g | 96% EtOH | 160 ml | 20 ml | r.t | 3 days | 1.24 | 6.2 |
| 20 g | 85% EtOH | 160 ml | 20 ml | r.t | 3 days | 1.93 | 9.7 |
| 20 g | 70% EtOH | 160 ml | 20 ml | r.t | 3 days | 1.96 | 9.8 |
| 20 g | 50% EtOH | 160 ml | 20 ml | r.t | 3 days | 2.28 | 11.4 |
| 20 g | 30% EtOH | 160 ml | 20 ml | r.t | 3 days | 2.37 | 11.9 |
| 20 g | 15% EtOH | 160 ml | 20 ml | r.t | 3 days | 3.1 | 15.5 |
| 20 g | 100% water | 160 ml | 20 ml | r.t | 3 days | 1.04 | 5.2 |

1-2. Preparation of an Extract of *Corydalis* Tuber

*Corydalis* Tuber was bought at a Chinese herb medicine shop of Kyung-dong market, washed by using water to remove adulterations, and dried to use in the experiment. And, the dried herb was milled by a mill, and 20 g of the milled *Corydalis* Tuber was put in 0%, 15%, 30%, 50%, 70%, 85% and 96% ethanol-water (160 ml) and stirred at room temperature for 72 h. Then, the resulting mixture was extracted, filtered, and concentrated at 55-65° C. under a low pressure, and freeze-dried by using the same method as Example 1-1 to obtain an extract of *Corydalis* Tuber (0.36~2.94 g)(Table 2: Yields of extracts of *Corydalis* Tuber as a kind of solvent).

TABLE 2

| Herb | Solvent | Amount of solvent | Wash | Extraction Temperature | Extraction Time | Obtained yield (g) | Yield (%) |
| --- | --- | --- | --- | --- | --- | --- | --- |
| 20 g | 96% EtOH | 160 ml | 20 ml | r.t | 3 days | 0.36 | 1.8 |
| 20 g | 85% EtOH | 160 ml | 20 ml | r.t | 3 days | 0.84 | 4.2 |
| 20 g | 70% EtOH | 160 ml | 20 ml | r.t | 3 days | 1.3 | 6.5 |
| 20 g | 50% EtOH | 160 ml | 20 ml | r.t | 3 days | 1.65 | 8.3 |
| 20 g | 30% EtOH | 160 ml | 20 ml | r.t | 3 days | 1.92 | 9.6 |
| 20 g | 15% EtOH | 160 ml | 20 ml | r.t | 3 days | 2.16 | 10.8 |
| 20 g | 100% | 160 ml | 20 ml | r.t | 3 days | 2.94 | 14.7 |

1-3. Preparation of an Extract of *Pharbitidis* Seed

*Pharbitidis* Seed was bought at a Chinese herb medicine shop of Kyung-dong market, washed by using water to remove adulterations, and dried to use in the experiment. And, the dried herb was milled by a mill, and 20 g of the milled *Pharbitidis* Seed was put in 0%, 15%, 30%, 50%, 70%, 85% and 96% ethanol-water (160 ml), and stirred at room temperature for 72 h. Then, the resulting mixture was extracted, filtered, and concentrated at 55~65° C. under a low pressure, and freeze-dried by using the same method as the Example 1-1 to obtain an extract of *Pharbitidis* Seed (0.92~3.85 g)(Table 3: Yields of extracts of *Pharbitidis* Seed as a kind of solvent).

TABLE 3

| Herb | Solvent | Amount of solvent | Wash | Extraction temperature | Extraction time | Obtained Amount (g) | Yield (%) |
| --- | --- | --- | --- | --- | --- | --- | --- |
| 20 g | 96% EtOH | 160 ml | 20 ml | r.t | 3 days | 0.92 | 4.6 |
| 20 g | 85% EtOH | 160 ml | 20 ml | r.t | 3 days | 1.03 | 5.2 |
| 20 g | 70% EtOH | 160 ml | 20 ml | r.t | 3 days | 1.27 | 6.4 |
| 20 g | 50% EtOH | 160 ml | 20 ml | r.t | 3 days | 2.13 | 10.7 |
| 20 g | 30% EtOH | 160 ml | 20 ml | r.t | 3 days | 2.14 | 10.7 |
| 20 g | 15% EtOH | 160 ml | 20 ml | r.t | 3 days | 3.85 | 19.3 |
| 20 g | 100% water | 160 ml | 20 ml | r.t | 3 days | 3.77 | 18.9 |

1-4. Preparation an Extract of *Strychnos ignatii* Semen

*Strychnos ignatii* Semen was bought at a Chinese herb medicine shop of Kyung-dong market, washed by using water to remove adulterations, and dried to use in the experiment. And, the dried herb was milled by a mill, and 20 g of the milled *Strychnos ignatii* Semen was put in 0%, 15%, 30%, 50%, 70%, 85% and 96% ethanol-water (160 ml) and stirred at room temperature for 72 h. Then, the resulting mixture was extracted, filtered, and concentrated at 55~65° C under a low pressure, and freeze-dried by using the same method as the Example 1-1 to obtain an extract of *Strychnos ignatii* Semen (0.59~5.41 g)(Table 3: Yields of extracts of *Strychnos ignatii* Semen as a kind of solvent).

TABLE 4

| Herb | Solvent | Amount of solvent | Wash | Extraction temperature | Extraction time | Obtained amount (g) | Yield (%) |
|---|---|---|---|---|---|---|---|
| 20 g | 96% EtOH | 160 ml | 20 ml | r.t | 3 days | 0.59 | 3.0 |
| 20 g | 85% EtOH | 160 ml | 20 ml | r.t | 3 days | 2.26 | 11.3 |
| 20 g | 70% EtOH | 160 ml | 20 ml | r.t | 3 days | 3.69 | 18.5 |
| 20 g | 50% EtOH | 160 ml | 20 ml | r.t | 3 days | 3.88 | 19.4 |
| 20 g | 30% EtOH | 160 ml | 20 ml | r.t | 3 days | 4.3 | 21.5 |
| 20 g | 15% EtOH | 160 ml | 20 ml | r.t | 3 days | 4.96 | 24.8 |
| 20 g | 100% water | 160 ml | 20 ml | r.t | 3 days | 5.41 | 27.1 |

EXAMPLE 2

Preparation a Soluble Extract in Polar Solvent and a Soluble Extract in Non-Polar solvent 2-1. Preparation of an Extract Soluble in Hexane 10 g of 50% ethanol extracts from Example 1 each were dissolved in 100 ml of a distilled water and 80 ml of methanol, put in a separatory funnel and, and mixed strongly to separate a water layer and a hexane layer. 180 ml of hexane was put again in the water-layer, mixed, and separated to obtain a soluble extract in hexane and an insoluble extract in hexane.

2-2. Preparation of an Extract Soluble in Chloroform

The insoluble extract in hexane (water-layer) was mixed with 160 ml of chloroform to separate a chloroform layer and a water layer. And, the water layer was added to 160 ml of chloroform, and mixed to obtain a soluble extract in chloroform and an insoluble extract in chloroform.

2-3. Preparation of an Extract Soluble in Ethylacetate

The insoluble extract in chloroform (water-layer) was mixed with 140 ml of ethylacetate to separate an ethylacetate layer and a water layer. And, the water layer was added to 140 ml of ethylacetate, and mixed to obtain a soluble extract in ethylacetate and an insoluble extract in ethylacetate.

2-4. Preparation of an Extract Soluble in Butanol

The insoluble extract in ethylacetate (water-layer) was mixed with 40 ml of butanol to separate a butanol layer and a water layer. And, the water layer was added to 20 ml of butanol, and mixed to obtain a soluble extract in butanol and an insoluble extract in butanol.

The extracts soluble in hexane, chloroform, ethylacetate and butanol, and the extracts insoluble in hexane, chloroform, ethylacetate and butanol were concentrated under a low pressure, and then freeze-dried to obtain an extract soluble in hexane (0.2~0.4 g), an extract soluble in chloroform (0.1~0.3 g), an extract soluble in ethylacetate (0.3~0.6 g), an extract soluble in butanol (0.8~1.6 g), and an extract soluble in water (1.5~3.0 g). The results were shown in Table 5 (The yield of extracts soluble in polar solvent and in non-polar solvent of various herbs)

TABLE 5

| Herb | Sequentially Fractional solvent | Amount of solvent | Extraction temperature | Obtained Amount (g) | Yield (%) |
|---|---|---|---|---|---|
| *Sinapis* Semen | Hexane | 180 ml × 2 | r.t* | 0.2 | 2 |
| (50% EtOH- | Chloroform | 160 ml × 2 | r.t | 0.24 | 2.4 |
| extract, 10 g) | Ethylacetate | 160 ml × 2 | r.t | 1.37 | 14 |
|  | Butanol | 40 ml, 20 ml | r.t | 0.22 | 2.2 |
| *Corydalis* | Hexane | 180 ml × 2 | r.t | 0.08 | 0.38 |
| Tuber | Chloroform | 160 ml × 2 | r.t | 0.86 | 2.9 |
| (50% EtOH | Ethylacetate | 160 ml × 2 | r.t | 1.17 | 12 |
| extract 10 g) | Butanol | 40 ml, 20 ml | r.t | 0.02 | 0.07 |
| *Pharbitidis* | Hexane | 180 ml × 2 | r.t | 0.20 | 2.0 |
| Seed | Chloroform | 160 ml × 2 | r.t | 0.11 | 1.1 |
| (50% EtOH | Ethylacetate | 160 ml × 2 | r.t | 0.32 | 3.2 |
| extract 10 g) | Butanol | 40 ml, 20 ml | r.t | 0.81 | 8.1 |
| *Strychni* | Hexane | 180 ml × 2 | r.t | 0.06 | 0.6 |
| *Ignatii* Semen | Chloroform | 160 ml × 2 | r.t | 0.87 | 8.7 |
| (50% EtOH | Ethylacetate | 160 ml × 2 | r.t | 0.52 | 5.2 |
| extract 10 g) | Butanol | 40 ml, 20 ml | r.t | — | — |

*r.t means room temperature.

EXAMPLE 3

Preparation of Mixtures of Herb Extracts of the Present Invention 3-1. Preparation of a Mixture of the Extracts of *Sinapis* Semen. *Corydalis* Tuber, and *Pharbitidis* Seed The 50% ethanol extracts obtained from Example 1 were mixed by the ratios of the extract of *Sinapis* Semen: the extract of *Corydalis* Tuber: the extract of *Pharbitidis* Seed to be 30:10:1, 30:3:1, 10:10:1, 10:3:1, 10:1:1, 3:3:1 and 3:1:1 weight in weight (w/w) to prepare 3-1-A, 3-1-B, 3-1-C, 3-1-D, 3-1-E, 3-1-F and 3-1-G as milled mixtures.

3-2. Preparation of a Mixture of the Extracts of *Sinapis* Semen and *Corydalis* Tuber The 50% ethanol extracts obtained from Example 1 were mixed by the ratios of the extract of *Sinapis* Semen and the extract of *Corydalis* Tuber to be 10:1, 3:1 and 1:1 weight in weight (w/w) to prepare 3-2-A, 3-2-B and 3-2-C as milled mixtures.

3-3. Preparation of a Mixture of the Extracts of *Sinapis* Semen and *Pharbitidis* Seed The 50% ethanol extracts obtained from Example 1 were mixed by the ratios of the extract of *Sinapis* Semen and the extract of *Pharbitidis* Seed to be 30:1, 10:1 and 3:1 weight in weight (w/w) to prepare 3-3-A, 3-3-B and 3-3-C as milled mixtures.

3-4. Preparation of a Mixture of the Extracts of *Corydalis* Tuber and *Pharbitidis* Seed The 50% ethanol extracts obtained from Example 1 were mixed by the ratios of the extract of *Corydalis* Tuber and the extract of *Pharbitidis* Seed to be 10:1, 3:1, and 1:1 weight in weight (w/w) to prepare 3-4-A, 3-4-B and 3-4-C as milled mixtures.

3-5. Preparation of a mixture of the extracts of *Corydalis* Tuber and *Strychni Ignatii* Semen The 50% ethanol extracts obtained from Example 1 were mixed by the ratios of the extract of *Corydalis* Tuber and the extract of *Strychni Ignatii* Semen to be 3:1, 1:1 and 1:3 weight in weight (w/w) to prepare 3-5-A, 3-5-B and 3-5-C as milled mixtures.

3-6. Preparation of a mixture of the extracts of *Pharbitidis* Seed and *Strychni Ignatii* Semen The 50% ethanol extracts obtained from Example 1 were mixed by the ratios of the extract of *Pharbitidis* Seed and the extract of *Strychni Ignatii* Semen to be 1:1, 1:3 and 1:10 weight in weight (w/w) to prepare 3-6-A, 3-6-B and 3-6-C as milled mixtures.

3-7. Preparation of a Mixture of the Extracts of *Sinapis* Semen. *Corydalis* Tuber *Pharbitidis* Seed, and *Strychni Ignatii* Semen The 50% ethanol extracts obtained from Example 1 were mixed by the ratios of the extract of *Sinapis* Semen: the extract of *Corydalis* Tuber: the extract of *Pharbitidis* Seed: the extract of *Strychni Ignatii* Semen to be 30:10:1:10, 30:10:1:3, 30:3:1:10, 30:3:1:3, 10:3:1:3, 10:10:1:10, 10:10:1:3, 10:3:1:10 and 3:3:1:3 weight in weight (w/w) to prepare 3-7-A, 3-7-B, 3-7-C, 3-7-D, 3-7-E, 3-7-F, 3-7-G, 3-7-H and 3-7-I as milled mixtures.

EXPERIMENTAL EXAMPLE 1

5-HT$_3$ receptor Binding assay on the extracts of Example 1

A binding assay was performed against Human-originated 5-HT$_3$ receptor for selecting a herbal extract having affinity for 5-HT$_3$ receptor [Nagakura Y et al., Pharmacology properties of a novel gastrointestinal prokinetics benzamide selective for human-5-HT4 receptor versus human 5-HT3 receptor. *Pharma. Research,* 39(5), pp. 375-382, 1999; Miyake et al., Molecular cloning of human 5-hydroxytamine3 receptor: heterogeneity in distribution and function among species. *Mol. Pharmacology*, pp. 407-416, 1995].

1-1. The Extract of *Sinapis* Semen

5-HT$_3$ receptor gene of sequence list No. 1 (HTR03A0000, UMR cDNA Resource Center) was transfected into Cos-7 cell to prepare a cell membrane of a developing receptor. The membrane (protein: 20 μg) was seeded to 96 well plate, and then an isotope-labeled ligand and the extract of *Sinapis* Semen were added to the plate, and mixed. After the plate was incubated at 25° C. for 40 min, the radioactivity of the plate was measured by beta radioactivity measuring instrument (top counter). The inhibition rates were calculated by using the following Math Figure 1.

$$\text{Inhibition ratio}(\%) = 100 - [(\text{searching substance CPM} - \text{non-specific binding CPM})/(\text{overall CPM} - \text{non-specific binding CPM}) \times 100] \qquad \text{[Math Figure 1]}$$

(*CPM: count per minute)

As shown in Table 6, the extract of *Sinapis* Semen from 50~96% ethanol-water showed the strongest affinity for 5-HT$_3$ receptor. The 50% inhibitive concentration (IC$_{50}$) of the extract of *Sinapis* Semen from 50% ethanol-water is 79.2 ug/ml (Table 7).

TABLE 6

|  | Concentration | Inhibition ratio (%) |
|---|---|---|
| 96% EtOH-extract of *Sinapis* Semen | 100 μg/ml | 95.5 |
|  | 300 μg/ml | 100.6 |
| 85% EtOH-extract of *Sinapis* Semen | 100 μg/ml | 88.4 |
|  | 300 μg/ml | 94.3 |
| 70% EtOH-extract of *Sinapis* Semen | 100 μg/ml | 87.6 |
|  | 300 μg/ml | 98.3 |
| 50% EtOH-extract of *Sinapis* Semen | 100 μg/ml | 73.3 |
|  | 300 μg/ml | 93.0 |
| 30% EtOH-extract of *Sinapis* Semen | 100 μg/ml | 52.3 |
|  | 300 μg/ml | 79.3 |
| 15% EtOH-extract of *Sinapis* Semen | 100 μg/ml | 33.2 |
|  | 300 μg/ml | 57.4 |
| Water-extract of *Sinapis* Semen | 100 μg/ml | 41.1 |
|  | 300 μg/ml | 54.9 |

TABLE 7

|  | Concentration (μg/ml) | Inhibition ratio (%) |
|---|---|---|
| 50% EtOH-extract | 10 | 1.0 |
|  | 30 | 8.0 |
|  | 100 | 60.0 |
|  | 300 | 89.7 |

1-2. The Extract of *Strychni Ignatii* Semen

The affinity of the extract of *Strychni Ignatii* Semen for 5-HT$_3$ receptor was measured by using the same method as the Experimental Example 1-1. The results were shown in Tables 8 and 9. As shown in Tables 8 and 9, the extracts of *Strychni Ignatii* Semen from 30~85% ethanol-water showed the strongest affinity for 5-HT$_3$ receptor. The 50% inhibitive concentration (IC$_{50}$) of the extract of *Strychni Ignatii* Semen from 50% ethanol-water is 144.9 ug/ml (Table 9).

TABLE 8

|  | Concentration | Inhibition ratio (%) |
|---|---|---|
| 96% EtOH-extract of *Strychni Ignatii* semen | 300 μg/ml | 77.8 |
|  | 1000 μg/ml | 79.8 |
| 85% EtOH-extract of *Strychni Ignatii* semen | 300 μg/ml | 70.2 |
|  | 1000 μg/ml | 93.6 |
| 70% EtOH-extract of *Strychni Ignatii* semen | 300 μg/ml | 67.6 |
|  | 1000 μg/ml | 89.0 |
| 50% EtOH-extract of *Strychni Ignatii* semen | 300 μg/ml | 72.6 |
|  | 1000 μg/ml | 87.6 |
| 30% EtOH-extract of *Strychni Ignatii* semen | 300 μg/ml | 70.8 |
|  | 1000 μg/ml | 87.5 |
| 15% EtOH-extract of *Strychni Ignatii* semen | 300 μg/ml | 60.4 |
|  | 1000 μg/ml | 80.0 |
| Water extract of *Strychni Ignatii* semen | 300 μg/ml | 66.4 |
|  | 1000 μg/ml | 86.1 |

TABLE 9

|  | Concentration (μg/ml) | Inhibition ratio (%) |
|---|---|---|
| 50%-ethanol extract | 30 | 20.0 |
|  | 100 | 40.0 |
|  | 300 | 69.3 |
|  | 1000 | 84.3 |

EXPERIMENTAL EXAMPLE 2

5-HT$_4$ receptor Binding assay of the extracts of Example 1

A binding assay was performed against human-originated 5-HT$_4$ receptor for selecting a herbal extract having affinity for 5-HT$_4$ receptor [Nagakura Y et al., Pharmacology properties of a novel gastrointestinal prokinetics benzamide selective for human-5-HT$_4$ receptor versus human 5-HT$_3$ receptor. *Pharma Research*, 39(5), pp. 375-382, 1999; Wyngaert I V et al., Cloning and expression of a human serotonin 5-HT4 receptor cDNA. *J. Neurochemistry*. 69(5), pp. 1810-1819, 1997].

2-1. The Extract of *Corydalis* Tuber

Figure 2:
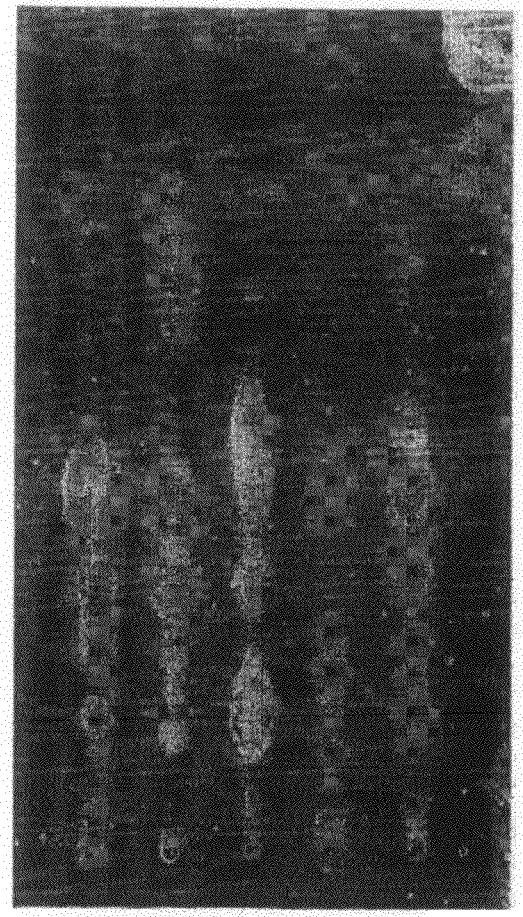
FIG. 2 is a schematic drawing illustrating the analytic results of thin liquid chromatography (TLC) of ethanol extracts of *Sinapis* Semen, *Corydalis* Tuber, *Pharbitidis* Seed and *Strychni Ignatii* Semen using $KMNO_4$.

5-HT$_4$ receptor gene of sequence list No. 2 (HTR0400000, UMR cDNA Resource Center) was transfected into Cos-7 cell to prepare a cell membrane as a developing receptor. The membrane (protein: 20 μg) was seeded to 96 well plate, and then an isotope-labeled ligand and the extract of *Corydalis* Tuber were added into the plate, and mixed. After the plate was incubated at 25° C. for 40 min, the radioactivity of the plate was measured by beta radioactivity measuring instrument (top counter). The inhibition rates were calculated by using the following Math Figure 2.

Inhibition ratio(%)=100−[(searching substance CPM−non-specific binding CPM)/(overall CPM−non-specific binding CPM)×100](*CPM: Count per minute) [Math Figure 2]

As shown in Tables 10 and 11, the extract of *Corydalis* Tuber from 50~96% ethanol-water showed the strongest affinity for 5-HT$_4$ receptor. The 50% inhibitive concentration (IC$_{50}$) of the extract of *Corydalis* Tuber from 50% ethanol-water is 43.4 ug/ml.

TABLE 10

|  | Concentration | Inhibition ratio (%) |
|---|---|---|
| 96% EtOH-extract of *Corydalis* Tuber | 100 μg/ml | 86.2 |
|  | 300 μg/ml | 99.5 |

TABLE 10-continued

|  | Concentration | Inhibition ratio (%) |
|---|---|---|
| 85% EtOH-extract of *Corydalis* Tuber | 100 μg/ml | 86.8 |
|  | 300 μg/ml | 99.6 |
| 70% EtOH-extract of *Corydalis* Tuber | 100 μg/ml | 81.1 |
|  | 300 μg/ml | 99.3 |
| 50% EtOH-extract of *Corydalis* Tuber | 100 μg/ml | 70.5 |
|  | 300 μg/ml | 99.7 |
| 30% EtOH-extract of *Corydalis* Tuber | 100 μg/ml | 60.0 |
|  | 300 μg/ml | 85.9 |
| 15% EtOH-extract of *Corydalis* Tuber | 100 μg/ml | 53.3 |
|  | 300 μg/ml | 80.2 |
| Water-extract of *Corydalis* Tuber | 100 μg/ml | 27.3 |
|  | 300 μg/ml | 77.2 |

TABLE 11

|  | Concentration (μg/ml) | Inhibition ratio (%) |
|---|---|---|
| 50%-ethanol extract | 10 | 22.3 |
|  | 30 | 37.7 |
|  | 100 | 65.1 |
|  | 300 | 94.9 |

2-2. The extract of *Pharbitidis* Seed

The affinity of the extract of *Pharbitidis* Seed for 5-HT$_3$ receptor was measured by using the same method as the Experimental Example 2-1. The results were shown in Tables 12 and 13. As shown in Tables 12 and 13, the extracts of *Pharbitidis* Seed from 50~96% ethanol-water showed the strongest affinity for 5-HT$_4$ receptor. The 50% inhibitive concentration (IC$_{50}$) of the extract of *Pharbitidis* Seed from 50% ethanol-water is 65.6 ug/ml.

TABLE 12

|  | Concentration | Inhibition ratio (%) |
|---|---|---|
| 96% EtOH extract of *Pharbitidis* Seed | 100 μg/ml | 61.2 |
|  | 300 μg/ml | 90.2 |
| 85% EtOH extract of *Pharbitidis* Seed | 100 μg/ml | 53.7 |
|  | 300 μg/ml | 90.3 |
| 70% EtOH extract of *Pharbitidis* Seed | 100 μg/ml | 67.1 |
|  | 300 μg/ml | 89.8 |
| 50% EtOH extract of *Pharbitidis* Seed | 100 μg/ml | 53.2 |
|  | 300 μg/ml | 87.4 |
| 30% EtOH extract of *Pharbitidis* Seed | 100 μg/ml | 47.5 |
|  | 300 μg/ml | 52.9 |
| 15% EtOH extract of *Pharbitidis* Seed | 100 μg/ml | 23.2 |
|  | 300 μg/ml | 48.5 |
| Water extract of *Pharbitidis* Seed | 100 μg/ml | 25.3 |
|  | 300 μg/ml | 44.7 |

TABLE 13

|  | Concentration (μg/ml) | Inhibition ratio (%) |
|---|---|---|
| 50% ethanol-extract | 10 | 11.4 |
|  | 30 | 20.7 |
|  | 100 | 66.0 |
|  | 300 | 84.9 |

EXPERIMENTAL EXAMPLE 3

5-HT$_3$ Receptor and 5-HT$_4$ Receptor Binding Assay of Soluble Extracts in Polar Solvent and in Non-Polar Solvent of Example 2

3-1. *Sinapis* Semen and *Strychni Ignatii* Semen

The affinities for 5-HT$_3$ receptor of the extracts extracted from hexane, chloroform, ethylacetate, and water of Example 2 were measured by a binding assay against human-originated 5-$HT_3$ receptor. The method of experiment was the same as the Experimental Example 1-1, and the extracts from polar solvent and from non-polar solvent had the concentrations shown in Table 14. As shown in Table 14, the extract (fraction) from chloroform was the most effective.

TABLE 14

|  | Concentration | Inhibition ratio (%) |
|---|---|---|
| Hexane-fraction of | 100 μg/ml | 1.3 |
| *Sinapis* Semen | 300 μg/ml | 4.6 |
| Chloroform-fraction of | 100 μg/ml | 63.9 |
| *Sinapis* Semen | 300 μg/ml | 87.3 |
| Ethylacetate-fraction of | 100 μg/ml | 59.3 |
| *Sinapis* Semen | 300 μg/ml | 79.0 |
| Water-fraction of | 100 μg/ml | 22.8 |
| *Sinapis* Semen | 300 μg/ml | 69.6 |
| Hexane-fraction of | 100 μg/ml | 1.9 |
| *Strychni Ignatii* Semen | 300 μg/ml | 1.8 |
| Chloroform-fraction of | 100 μg/ml | 70.5 |
| *Strychni Ignatii* Semen | 300 μg/ml | 90.6 |
| Ethylacetate-fraction of | 100 μg/ml | 19.0 |
| *Strychni Ignatii* Semen | 300 μg/ml | 45.6 |
| Water-fraction of | 100 μg/ml | 6.0 |
| *Strychni Ignatii* Semen | 300 μg/ml | 27.5 |

3-2. *Corydalis* Tuber and *Pharbitidis* Seed

The affinities for 5-$HT_4$ receptor of the extracts extracted from hexane, chloroform, ethylacetate and water of Example 2 were compared. The method of experiment was the same as the Experimental Example 1-1. As shown in Table 15, the extract (fraction) from chloroform was the most effective.

TABLE 15

|  | Concentration | Inhibition ratio (%) |
|---|---|---|
| Hexane-fraction of | 100 μg/ml | 0.3 |
| *Corydalis* Tuber | 300 μg/ml | 21.0 |
| Chloroform-fraction of | 100 μg/ml | 86.8 |
| *Corydalis* Tuber | 300 μg/ml | 99.6 |
| Ethylacetate-fraction of | 100 μg/ml | 44.9 |
| *Corydalis* Tuber | 300 μg/ml | 79.7 |
| Water-fraction of | 100 μg/ml | 34.5 |
| *Corydalis* Tuber | 300 μg/ml | 45.4 |
| Hexane-fraction of | 100 μg/ml | 41.9 |
| *Pharbitidis* Seed | 300 μg/ml | 53.8 |
| Chloroform-fraction of | 100 μg/ml | 68.9 |
| *Pharbitidis* Seed | 300 μg/ml | 74.1 |
| Ethylacetate-fraction of | 100 μg/ml | 52.6 |
| *Pharbitidis* Seed | 300 μg/ml | 34.2 |
| Water-fraction of | 100 μg/ml | 48.0 |
| *Pharbitidis* Seed | 300 μg/ml | 57.1 |

EXPERIMENTAL EXAMPLE 4

Antagonistic Effect of the Extracts of Example 1 on 5-$HT_3$

Receptors Using The Colon Of Guinea Pig

An organ bath experiment was performed by using the colon of guinea pig and the extracts from 50% ethanol of the Example 1 to measure the antagonistic effects of the extracts on 5-$HT_3$ receptor (Briejer M et al., The in vitro pharmacological profile of prucalopride, a novel enterokinetic compound. *European Journal of Pharmacology* 423, pp. 71-83, 2001).

Laparotomy was performed to extirpate the colon of guinea pig after $CO_2$ asphyxiation. And, the extirpated colon with a parallel two stirrup was fixed.

The colon was stabilized at least for 30 min before treated with the extracts, and gradually the tension of the colon became 1 g (the tension before loading the sample is 0.0 g). For response of the extracts, methacholine (3 μM) was added to the colon to induce contraction of the colon. And, the colon was stabilized for 15 min, treated with the extracts to make each sample to have the same concentration, and cultured for 15 min. After 0.1 μM of serotonin (5-HT) was treated thereto, the contraction of the colon was checked, and then the colon was washed out, and treated with the extracts repeatedly to prepare a sample and 0.3 μM of serotonin (5-HT). The inhibitive effects of the sample after treated with 0.1, 0.3, 1, 3, 10 and 30 μM of serotonin (5-$HT_3$) by repeatedly using the method are shown in the following Table 16. The value of $IC_{50}$ of the extract of *Pharitidis* seed from 50% ethanol-water was 27.8 ug/ml, and that of the extract of *Corydalis* Tuber from an 50% ethanol-water was 76.5 ug/ml, and that of the extract of *Strychni Ignatii* Semen from an 50% ethanol-water was 138.7 ug/ml.

TABLE 16

|  | Inhibition ratio for a 5-HT induced contract (%) | | | |
|---|---|---|---|---|
| Concentration | *Sinapis* Semen | *Corydalis* Tuber | *Pharbitidis* Seed | *Strychni Ignatii* Semen |
| 30 μg/ml | 4.4 | 30.4 | 73.3 | −13.6 |
| 100 μg/ml | 20.5 | 59.0 | 90.0 | 34.8 |
| 300 μg/ml | 32.5 | 84.0 | 93.0 | 93.0 |

EXPERIMENTAL EXAMPLE 5

Agonistic Effect of the Extracts of Example 1 on 5-$HT_4$ Receptors Using the Oesophagus Segment of Wister Male Rats An organ bath experiment was performed to the oesophagus segment of Wister male rats, and the extracts from 50% ethanol of Example 1 to measure the agonistic effect of the extracts on 5-$HT_4$ receptors. The measuring method was disclosed in the document of Briejer M et al. (The in vitro pharmacological profile of prucalopride, a novel enterokinetic compound. *European Journal of Pharmacology*, 423, pp. 71-83, 2001; Sonda S et al., Synthesis and pharmacological properties of benzamide derivatives as selective serotonin 4 receptor agonists. *Bioorganic & Medicinal Chemistry*, 12, pp. 2737-2747, 2004).

Laparotomy was performed to extirpate the oesophagus of SD rat after $CO_2$ asphyxiation. The extirpated colon with a parallel two stirrup was fixed.

The colon was stabilized at least for 60 min before treated with the extracts, and gradually the tension of the oesophagus became 1 g (the tension before loading the sample is 0.0 g) for early 30 min. For response of the extracts, carbachol (3 μM) was added to the oesophagus to induce contraction, and the oesophagus was stabilized, and then treated with 0.1, 0.3, 1, 3, 10, 30 μM of serotonin (5-HT) to set the maximum relaxation strength 100% at this time. After the oesophagus was washed out, the solution was changed for stabilization for 1 hour at 15 min interval. Then, the oesophagus was treated with carbachol (3 μM) to induce contraction, and stabilized. And, the contractive effects of the oesophagus were measured after treated with 3, 10, 30, 100, 300 μg/ml of the extracts. At this time, only the extracts showing the contractive effect to the oesophagus were treated after they were treated with GR13808 (30 nM), and the agonistic effects of the extracts on a 5-HT$_4$ receptor were measured. The results are shown in the following Table 17.

The values of EC$_{50}$ (median effective concentration) of the extract of *Corydalis* Tuber from 50% ethanol-water was 12.1 ug/ml, and that of the extract of *Pharitidis* seed from 50% ethanol-water was 67.4 ug/ml, and that of the extract of *Strychni Ignatii* Semen from 50% ethanol-water was 38.8 ug/ml.

TABLE 17

| Concentration | Reactivity by the change of a concentration (%) | | | |
|---|---|---|---|---|
| | *Sinapis* Semen | *Corydalis* Tuber | *Pharbitidis* Seed | *Strychni Ignatii* Semen |
| 3 µg/ml | 11.0 | 23.9 | 5.9 | 12.3 |
| 10 µg/ml | 16.8 | 37.9 | −14.2 | 21.9 |
| 30 µg/ml | 26.6 | 55.3 | 24.2 | 34.1 |
| 100 µg/ml | 38.0 | 76.3 | 55.1 | 50.8 |
| 300 µg/ml | 74.0 | 129.3 | 95.0 | 101.6 |

EXPERIMENTAL EXAMPLE 6

Confirmation of Delayed Gastric Emptying Effect of the Extracts of the Present Invention The delayed gastric emptying effects of the extracts from 50% ethanol-water in Example 1 and the mixtures of Example 3 were measured by using delayed gastric emptying model (Ozaki A and Sukamoto et al., Improvement of cisplatin-induced emesis and delayed gastric emptying by KB-R6933, a novel 5-HT3 receptor antagonist. General pharmacology, 33, pp. 283-288, 1999).

Figure 3:
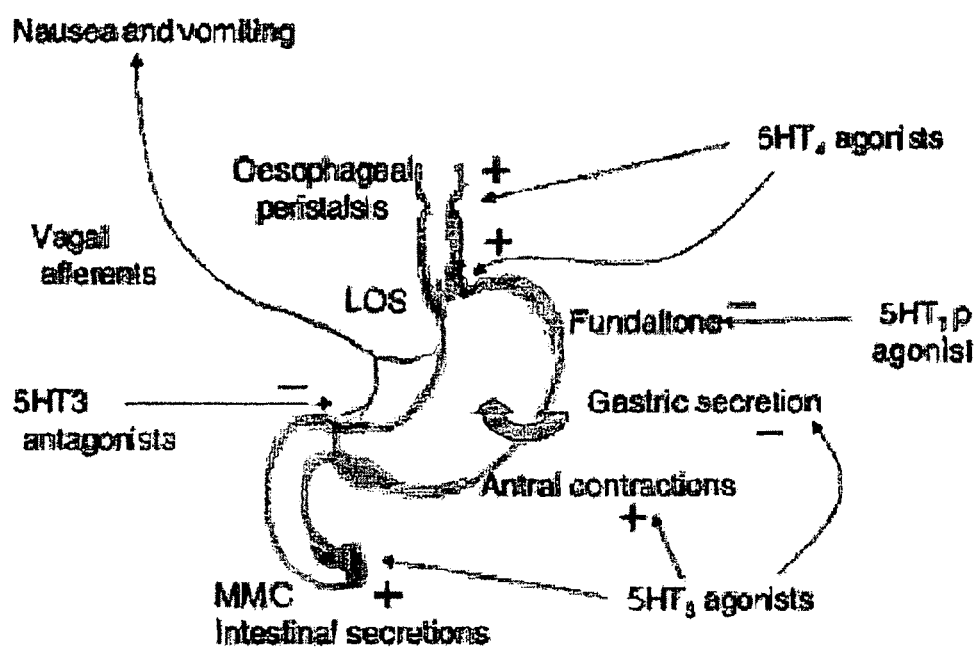
FIG. 3 is a schematic drawing illustrating multi activities of agonist for 5-$HT_3$ receptor.

200~250 g of male SD rats were bred with supplying standard food and water at 22-24° C. and 60~80 RH % (relative humidity %) for 1 week. And, the rats were divided by the weight, and starved for 24 hours. Each of the extracts were dissolved in physiological salt solution fixed dosage or Hydroxypropylmethylcellulose (HPMC, 3%), and the solution was administrated orally to the rats. After 60 min, 10 mg/kg of cisplatin (dissolved in physiological salt solution at 50° C. and cooled at 37° C. at the administration) was administered to an abdominal cavity of the rats. And, 1.5 ml of semisolid test meal (0.05% phenol red solution containing 1.5% MC) were orally administered to each rat. After 15~30 min, the rats were killed to remove the stomach, and the amount of the remained phenol red in the stomach was measured. The stomach and contents were dissolved in 100 ml of 0.1N NaOH solution for 20 seconds, and were left at room temperature for 1 hour. And, 5 ml of the homogenate was moved to tube. Then, 0.5 ml of trichloroacetic acid (20%) was added to the tube for protein precipitation, and the tube was centrifuged at 2500×g for 20 min. And, 2 ml of 0.5N NaOH solution was added thereto as equivalent liquid, and the absorbance was measured at 560 nm (ABS$_{560\ nm}$). The gastric emptying rate was calculated by the following Math Figure 3.

$$\text{Gastric emptying}(\%) = [1 - (B/A)] \times 100 \quad \text{[Math Figure 3]}$$

A: The whole amount of phenol red recovered from the stomach immediately after the phenol red administration B: The amount of phenol red remaining in the stomach after the phenol red administration The results about delayed gastric emptying effects of the extracts and mixtures thereof were shown in the following Tables 18 and 19. Each extract showed the delayed gastric emptying effect (Table 18), and the mixtures of the extracts showed the delayed gastric emptying effect (Table 19). Particularly, the mixture of the extracts of *Corydalis* Tuber and *Pharitidis* seed, and the mixture of the extracts of *Corydalis* Tuber and *Strychni Ignatii* Semen were the most effective.

1) The Delayed Gastric Emptying Effect of the Extracts

TABLE 18

| | Dosage (mg/kg) | Gastric emptying ratio (%) |
|---|---|---|
| Normal | — | 84.4 |
| Control | — | 54.6 |
| *Sinapis* Semen | 1 | 50.7 |
| | 10 | 67.9 |
| | 30 | 81.7 |
| | 100 | 81.5 |
| Normal | — | 68.4 |
| Control | — | 43.2 |
| *Corydalis* Tuber | 1 | 38.6 |
| | 10 | 64.7 |
| | 30 | 64.5 |
| | 100 | 63.7 |
| Normal | — | 79.3 |
| Control | — | 43.0 |
| *Pharbitidis* Seed | 1 | 40.6 |
| | 3 | 73.2 |
| | 10 | 72.8 |
| | 30 | 70.3 |
| Normal | — | 85.2 |
| Control | — | 68.8 |
| *Strychni Ignatii* Semen | 3 | 72.3 |
| | 10 | 85.9 |
| | 30 | 85.4 |

In the above table, 'normal' represents a normal group without cisplatin and the extract of the present invention, and 'control' represents a positive control group with a physiological salt solution.

2) The Delayed Gastric Emptying Effect of the Mixtures of the Extracts

TABLE 19

| | Mixed ratio | Dosage (mg/kg) | Gastric emptying ratio (%) |
|---|---|---|---|
| Normal | | | 90.2 |
| Control | | | 69.0 |
| *Sinapis* Semen + *Corydalis* Tuber +*Pharbitidis* Seed + *Strychni Ignatii* Semen | 30:10:1:10 | 40 | 69.0 |
| | 30:10:1:3 | 40 | 86.7 |
| | 30:3:1:10 | 40 | 88.0 |
| | 30:3:1:3 | 40 | 89.0 |
| | 10:3:1:3 | 40 | 88.7 |
| | 10:10:1:10 | 40 | 85.2 |
| | 10:10:1:3 | 40 | 85.9 |
| | 10:3:1:10 | 40 | 87.1 |
| | 3:3:1:3 | 40 | 87.8 |
| *Sinapis* Semen + *Corydalis* Tuber + *Pharbitidis* Seed | 30:10:1 | 30 | 77.7 |
| | 30:3:1 | 30 | 89.1 |
| | 10:10:1 | 30 | 78.2 |
| | 10:3:1 | 30 | 89.0 |
| | 10:1:1 | 30 | 76.9 |
| | 3:3:1 | 30 | 85.6 |
| | 3:1:1 | 30 | 79.8 |
| *Sinapis* Semen + *Corydalis* Tuber | 10:1 | 10 | 77.2 |
| | 3:1 | 10 | 84.1 |
| | 1:1 | 10 | 76.9 |
| *Sinapis* Semen + *Pharbitidis* Seed | 30:1 | 10 | 78.2 |
| | 10:1 | 10 | 89.3 |
| | 3:1 | 10 | 77.9 |
| *Corydalis* Tuber + *Pharbitidis* Seed | 10:1 | 10 | 89.1 |
| | 3:1 | 10 | 95.4 |
| | 1:1 | 10 | 92.5 |
| *Corydalis* Tuber + *Strychni Ignatii* Semen | 3:1 | 10 | 89.4 |
| | 1:1 | 10 | 90.1 |
| | 1:3 | 10 | 89.9 |
| *Pharbitidis* Seed + *Strychni Ignatii* Semen | 1:1 | 10 | 88.5 |
| | 1:3 | 10 | 89.0 |
| | 1:10 | 10 | 87.2 |

In the above table, 'normal' represents a normal group without cisplatin and an extract of the present invention, and 'control' represents a positive control group with a physiological salt solution.

EXPERIMENTAL EXAMPLE 7

Confirmation of the Semi-Solid Gastric Emptying Delaying Effect of the Extracts of the Present Invention The semi-solid gastric emptying effects of the extracts from 50% ethanol-water in Example 1 and the mixtures of Example 3 were measured by using semi-solid gastric emptying model (Calatayud S, Garcia-Zaragoza E, Hernandez C, Quintana E, Felipo V, Esplugues J V, Barrachina M D. Downregulation of nNOS and synthesis of PGs associated with endotoxin-induced delay in gastric emptying. Am J Physiol Gastrointest Liver Physiol. 2002 December; 283(6):G1360-7).

200~250 g of male SD rats were bred with supplying standard food and water at 22-24° C. and 60~80 RH % (relative humidity %) for 1 week. And, the rats were divided by the weight, and starved for 24 hours. During the starving time, drinking water was supplied, but the supplying was stopped 3 hours before the experiment. Each extract was dissolved in physiological salt solution fixed dosage or Hydroxypropyl-methylcellulose (HPMC, 3%), and the solution was administrated orally to the rat. After 45 min, 2 ml of semisolid test meal (0.05% phenol red solution containing 1.5% MC) made by crushing down an animal food dissolved in water was orally administered to each rat. After 35 min, the rats were killed to remove the stomach, and the stomach having semi-solid test meal weighed. The gastric emptying rates were calculated by the following Math Figure 4.

Gastric emptying(%)=[1−(weight of semisolid meal remained in stomach/weight of semisolid meal remained in 0 hour's stomach)]×100  [Math Figure 4]

("Weight of semisolid meal remained in 0 hour's stomach" is measured from remained semisolid meal obtained from the stomach immediately after it's administration)

The results about the gastric emptying delaying effects of the extracts and their mixtures were shown in the following Tables 20 and 21. Each extract showed the gastric emptying delaying effect (Table 20), and the mixture of extracts showed the more effective gastric emptying delaying effect (Table 21) than the extracts. Particularly, the mixture of the extracts of *Corydalis* Tuber and *Pharitidis* seed, and the mixture of the extracts of *Corydalis* Tuber and *Strychni Ignatii* Semen were the most effective.

1) The Semi-Solid Gastric Emptying Effect of the Extracts

TABLE 20

| | Dosage (mg/kg) | Gastric emptying ratio (%) |
|---|---|---|
| Control | — | 31.5 |
| *Sinapis* Semen | 1 | 36.0 |
| | 10 | 36.2 |
| | 30 | 47.3 |
| | 100 | 44.4 |
| Control | — | 34.1 |
| *Corydalis* Tuber | 1 | 38.7 |
| | 10 | 55.6 |
| | 30 | 47.4 |
| | 100 | 48.6 |

TABLE 20-continued

| | Dosage (mg/kg) | Gastric emptying ratio (%) |
|---|---|---|
| Control | — | 33.0 |
| *Pharbitidis* Seed | 0.3 | 35.6 |
| | 1 | 45.6 |
| | 3 | 53.2 |
| | 10 | 37.5 |
| Control | — | 35.4 |
| *Strychni Ignatii* Semen | 1 | 38.4 |
| | 3 | 42.7 |
| | 10 | 53.0 |

In the above table, 'control' means control group to which a physiological salt solution instead of the extract is administered.

2) The Semi-Solid Gastric Emptying Effect of the Mixtures of Extracts

TABLE 21

| | Mixed ratio | dosage (mg/kg) | Gastric emptying ratio (%) |
|---|---|---|---|
| Control | | | 20.4 |
| *Sinapis* Semen + *Corydalis* Tuber + *Pharbitidis* Seed + *Strychni Ignatii* Semen | 30:10:1:10 | 40 | 48.9 |
| | 30:10:1:3 | 40 | 49.0 |
| | 30:3:1:10 | 40 | 50.8 |
| | 30:3:1:3 | 40 | 53.2 |
| | 10:3:1:3 | 40 | 52.8 |
| | 10:10:1:10 | 40 | 44.4 |
| | 10:10:1:3 | 40 | 47.6 |
| | 10:3:1:10 | 40 | 48.5 |
| | 3:3:1:3 | 40 | 52.1 |
| *Sinapis* Semen + *Corydalis* Tuber + *Pharbitidis* Seed | 30:10:1 | 30 | 47.3 |
| | 30:3:1 | 30 | 51.2 |
| | 10:10:1 | 30 | 48.0 |
| | 10:3:1 | 30 | 49.4 |
| | 10:1:1 | 30 | 45.7 |
| | 3:3:1 | 30 | 50.5 |
| | 3:1:1 | 30 | 44.5 |
| *Sinapis* Semen + *Corydalis* Tuber | 10:1 | 10 | 45.6 |
| | 3:1 | 10 | 42.7 |
| | 1:1 | 10 | 48.5 |
| *Sinapis* Semen + *Pharbitidis* Seed | 30:1 | 10 | 48.2 |
| | 10:1 | 10 | 47.5 |
| | 3:1 | 10 | 43.0 |
| *Corydalis* Tuber + *Pharbitidis* Seed | 10:1 | 10 | 54.5 |
| | 3:1 | 10 | 57.8 |
| | 1:1 | 10 | 44.5 |
| *Corydalis* Tuber + *Strychni Ignatii* Semen | 3:1 | 10 | 48.3 |
| | 1:1 | 10 | 50.3 |
| | 1:3 | 10 | 40.2 |
| *Pharbitidis* Seed + *Strychni Ignatii* Semen | 1:1 | 10 | 45.8 |
| | 1:3 | 10 | 49.8 |
| | 1:10 | 10 | 42.9 |

In the above table, 'control' means control group to which a physiological salt solution instead of the extract is administered.

EXPERIMENTAL EXAMPLE 8

Confirmation of the Upper Gastrointestinal Motility Effect of the Extracts of the Present Invention The upper gastrointestinal motility effect of the extracts from 50% ethanol-water in Example 1 and the mixtures of Example 3 were measured.

220~230 g of male SD rats were bred with supplying standard food and water at 22-24° C. and 60~80 RH % (relative humidity %) for 1 week. And, the rats were divided by the weight, and the rats were starved for 24 hours. For inhibiting the upper gastrointestinal motility effect, 1 mg/kg of atropine (dissolved in physiological salt solution at 50° C. and cooled at 37° C. at the administration) was administrated to the rat's abdominal cavity. Then, each extract's fixed dosage was dissolved in physiological salt solution or Hydroxypropylmethylcellulose (HPMC, 3%), and the solution was administrated orally to the rats. After 1 hour, 1 ml of fluorescein isocyanate-labeled dextran (FITC)(used 5 mM of FITC solution diluted up to 10 times in physiological salt solution) was administered to each rat. After 15 min, autopsy was done to the rats. And, a small intestine from the portio pyorica ventriculi to the appendix was cut equally to 10 pieces. The tissues were soaked in 1 ml of physiological salt solution, and left in a refrigerator. After 1 day, the fluorescence of each equivalent liquid was detected. The distribution ratio of fluorescein isocyanate-labeled dextran in the small intestine was obtained by using the Math Figure 5 from the detected values, and the motility of a gastrointestinal tract represented to a geometric center to the distribution of fluorescein isocyanate-labeled dextran. And, the stomach was separated, and weighed to measure the gastric emptying.

1) Fraction of fluorescence per segment=(fluorescence of each segment/overall)×100

2) Geometric center=[Σ(fraction of fluorescence per segment×segment number)]/100    [Math Figure 5]

The effects of the gastrointestinal motility to each herbal extract and mixtures thereof were shown in the following Table 22 (The delayed effect of gastrointestinal motility effect of extracts of the present invention) and Table 23 (The gastric emptying effect in the delayed model of gastrointestinal motility effect of extracts of the present invention). It was confirmed that the mixtures of herbal extracts are more effective than the herbal extracts.

TABLE 22

|  | Herb | Dosage (Mixed ratio) | Geometric center |
|---|---|---|---|
| Control | — | — | 3.46 |
| A herbal extract | *Sinapis* Semen | 30 | 3.62 |
|  | *Corydalis* Tuber | 30 | 4.25 |
|  | *Pharbitidis* Seed | 3 | 3.54 |
|  | *Strychni Ignatii* Semen | 10 | 3.96 |
| Control | — | — | 3.32 |
| A mixture of herb extracts | *Sinapis* Semen + *Corydalis* Tuber + *Pharbitidis* Seed + *Strychni Ignatii* Semen | 40 (30:3:1:3) | 4.04 |
|  | *Sinapis* Semen + *Corydalis* Tuber + *Pharbitidis* Seed | 30 (30:3:1) | 3.66 |
|  | *Sinapis* Semen + *Corydalis* Tuber | 10 (10:1) | 3.66 |
|  | *Sinapis* Semen + *Pharbitidis* Seed | 10 (30:1) | 3.58 |
|  | *Corydalis* Tuber + *Pharbitidis* Seed | 10 (3:1) | 4.09 |
|  | *Corydalis* Tuber +*Strychni Ignatii* Semen | 10 (1:1) | 3.66 |
|  | *Pharbitidis* Seed + *Strychni Ignatii* Semen | 10 (1:3) | 3.58 |
| Control | — | — | 3.32 |
| A mixture of herb extracts | *Corydalis* Tuber + *Pharbitidis* Seed | 0.3 (3:1) | 3.50 |
|  |  | 1 (3:1) | 4.09 |
|  |  | 3 (3:1) | 3.66 |
|  |  | 10 (3:1) | 3.66 |
|  |  | 30 (3:1) | 3.58 |

At the above table, "control" means a positive control group treated with a physiological salt solution instead of the extract.

TABLE 23

|  | Herb | Dosage (mixed ratio) | Gastric emptying ratio (%) |
|---|---|---|---|
| Control | — | — | 52.8 |
| A herbal extract | *Sinapis* Semen | 30 | 64.94 |
|  | *Corydalis* Tuber | 30 | 75.89 |
|  | *Pharbitidis* Seed | 3 | 59.48 |
|  | *Strychni Ignatii* Semen | 10 | 65.17 |
| Control | — | — | 48.28 |
| A mixture of herbal extracts | *Sinapis* Semen + *Corydalis* Tuber + *Pharbitidis* Seed + *Strychni Ignatii* Semen. | 40 (30:3:1:3) | 70.52 |
|  | *Sinapis* Semen + *Corydalis* Tuber + *Pharbitidis* Seed | 30 (30:3:1) | 73.63 |
|  | *Sinapis* Semen + *Corydalis* Tuber | 10 (10:1) | 68.51 |
|  | *Sinapis* Semen + *Pharbitidis* Seed | 10 (30:1) | 63.58 |
|  | *Corydalis* Tuber + *Pharbitidis* Seed | 10 (3:1) | 81.72 |
|  | *Corydalis* Tuber + *Strychni Ignatii* Semen | 10 (1:1) | 73.66 |
|  | *Pharbitidis* Seed + *Strychni Ignatii* Semen | 10 (1:3) | 73.58 |
| Control | — | — | 48.28 |
| A mixture of herbal extracts | *Corydalis* Tuber + *Pharbitidis* Seed | 0.3 (3:1) | 71.60 |
|  |  | 1 (3:1) | 82.73 |
|  |  | 3 (3:1) | 80.51 |
|  |  | 10 (3:1) | 73.18 |
|  |  | 30 (3:1) | 64.80 |

At the above table, "control" means a positive control group treated with a physiological salt solution instead of the extract.

The following preparation examples contain one or more extracts selected from the group consisting of *Sinapis* Semen, *Corydalis* Tuber, *Pharbitidis* Seed and *Strychni Ignatii* Semen of the present invention. But, the preparation examples intended only to explain the present invention in the concrete manner, and are not intended to limit the scope of the present invention in any way.

PREPARATION EXAMPLE 1

Preparation of an Injectable Dosage Form

The extracts of Example 1 . . . 100 mg
Sodium metabisulphite . . . 3.0 mg
Methylparaben . . . 0.8 mg
Propylparaben . . . 0.1 mg
Injectable distilled water . . . Proper quantity
The ingredients were mixed and made to 2 ml of total volume by a method known in the art. And, the mixture was filled into an ample of 2 ml dose, and sterilized to prepare an injectable dosage form

PREPARATION EXAMPLE 2

Preparation of an Injectable Dosage Form

The extracts of Example 2 . . . 1030 mg
Sodium metabisulphite . . . 3.0 mg
Methylparaben . . . 0.8 mg
Propylparaben . . . 0.1 mg
Injectable distilled water . . . Proper quantity
The ingredients were mixed and made to 2 ml of total volume by a method known in the art. And, the mixture was filled into an ample of 2 ml dose, and sterilized to prepare an injectable dosage form.

PREPARATION EXAMPLE 3

Preparation of an Injectable Dosage Form

The extracts of Example 3 . . . 100~300 mg
Sodium metabisulphite . . . 3.0 mg
Methylparaben . . . 0.8 mg
Propylparaben . . . 0.1 mg
Injectable distilled water . . . Proper quantity
The ingredients were mixed and made to 2 ml of total volume by a method known in the art. And, the mixture was filled into an ample of 2 ml dose, and sterilized to prepare an injectable dosage form.

PREPARATION EXAMPLE 4

Preparation of a tablet

The extracts of Example 1 . . . 100~300 mg
Lactose . . . 100 mg
Starch . . . 100 mg
Magnesium stearate . . . Proper quantity
The ingredients were mixed and made to a tablet by a tablet preparation method known in the art.

PREPARATION EXAMPLE 5

Preparation of a Tablet

The extracts of Example 2 . . . 10~30 mg
Lactose . . . 100 mg
Starch . . . 100 mg
Magnesium stearate . . . Proper quantity
The ingredients were mixed and made to a tablet by a tablet preparation method known in the art.

PREPARATION EXAMPLE 6

Preparation of a Tablet

The extracts of Example 3 . . . 100~1000 mg
Lactose . . . 100 mg
Starch . . . 100 mg
Magnesium stearate . . . Proper quantity
The ingredients were mixed and made to a tablet by a tablet preparation method known in the art.

PREPARATIVE EXAMPLE 7

Preparation of a Capsule

The extracts of Example 1 . . . 100~300 mg
Lactose . . . 50 mg
Starch . . . 50 mg
talc . . . 2 mg
Magnesium stearate . . . Proper quantity
The ingredients were mixed and filled into a gelatin capsule by a capsule preparation method known in the art to prepare the capsule.

PREPARATIVE EXAMPLE 8

Preparation of a Capsule

The extracts of Example 2 . . . 10~30 mg
Lactose . . . 50 mg
Starch . . . 50 mg
talc . . . 2 mg
Magnesium stearate . . . Proper quantity
The ingredients were mixed and filled into a gelatin capsule by a capsule preparation method known in the art to prepare the capsule.

PREPARATIVE EXAMPLE 9

Preparation of a Capsule

The extracts of Example 3 . . . 100~1000 mg
Lactose . . . 50 mg
Starch . . . 50 mg
talc . . . 2 mg
Magnesium stearate . . . Proper quantity
The ingredients were mixed and filled into a gelatin capsule by a capsule preparation method known in the art to prepare the capsule.

PREPARATION EXAMPLE 10

Preparation of Liquid Formulation

The extracts of Example 1 . . . 100~300 mg
Sugar . . . 20 g
Isomerized sugar . . . 20 g
Lemon spices . . . Proper quantity
Purified water . . . Quantity to make the
total volume of the liquid formulation to 100 ml
The ingredients were mixed by a preparing method for liquid formulation known in the art, filled into a brown bottle of 100 ml, and sterilized to prepare a liquid formulation.

PREPARATION EXAMPLE 11

Preparation of Liquid Formulation

The extracts of Example 2 . . . 10~30 mg
Sugar . . . 20 g
Isomerized sugar . . . 20 g
Lemon spices . . . Proper quantity
Purified water . . . Quantity to make the
total volume of liquid formulation to 100 ml
The ingredients were mixed by a preparing method for liquid formulation known in the art, filled into a brown bottle of 100 ml, and sterilized to prepare a liquid formulation.

PREPARATION EXAMPLE 12

Preparation of Liquid Formulation

The extracts of Example 3 . . . 100~1000 mg
Sugar . . . 20 g
Isomerized sugar . . . 20 g
Lemon spices . . . Proper quantity
Purified water . . . Quantity to make the
total volume of liquid formulation to 100 ml
The ingredients were mixed by a preparing method for liquid formulation known in the art, filled into a brown bottle of 100 ml, and sterilized to prepare a liquid formulation.

Industrial Applicability

The extracts of the present invention or mixtures thereof may be used as a pharmaceutical composition for preventing and treating gastrointestinal motility disorder, and a health functional food since it can facilitate gastrointestinal motility as their $HT_3$ receptor antagonism and/or $HT_4$ receptor agonism.

What is claimed is:

1. A mixture of herbal extracts consisting of an extract of *Corydalis* Tuber and an extract of *Pharbitidis* Seed in a ratio of the extract of *Corydalis* Tuber to the extract of *Pharbitidis* Seed from 1:1 to 10:1 (w/w).

2. The mixture of herbal extracts of claim 1, wherein the herbal extracts are extracted by water, a lower alcohol of C1-C4, or a mixed solvent thereof.

3. A method for preparing the mixture of herbal extracts of claim 1 comprising extracting dried *Corydalis* Tuber and *Pharbitidis* Seed by using water, a lower alcohol of C1-C4, or a mixture thereof from one to five times at 45-75° C. for 65-80 hours.

4. A composition for treating gastrointestinal motility disorder consisting of the mixture of herbal extracts of claim 1 as an active ingredient and a pharmaceutically acceptable carrier.

5. The composition of claim 4, wherein the gastrointestinal motility disorder is a disorder originated from hyperactivity of 5-HT3 receptor and/or 5-HT4 receptor antagonism.

6. The composition of claim 5, wherein the gastrointestinal motility disorder is a disorder selected from the group consisting of functional dyspepsia such as early satiety, pain, epigastric distress, a false sense of satiety, heartburn, nausea and vomiting; ulcerative dyspepsia, non-ulcerative dyspepsia; reflux oesophagitis, paralysis of gastric motility; constipation; irritable bowel syndrome; hypersensitive colitis; diabetic gastrointestinal motility disorder; gastrointestinal motility disorder originated chemotherapy; and intestinal atresia originated motility disorder of digestive tract and myotonic dystrophy originated gastric intestinal disorder.

7. A health care food for improving gastrointestinal motility disorder consisting of the mixture of herbal extracts of claim 1 as an active ingredient and a sitologically acceptable carrier.

8. The health care food of claim 7, wherein the food is powder, granule, tablet, capsule, syrup or beverage.

* * * * *